(12) United States Patent
Johannes et al.

(10) Patent No.: US 7,433,449 B2
(45) Date of Patent: Oct. 7, 2008

(54) APPARATUS FOR DRIVING A SCATTERED RADIATION GRID OF A DIAGNOSTIC X-RAY SYSTEM

(75) Inventors: Reger Johannes, Erbendorf (DE); Trottmann Jürgen, Falkenberg (DE)

(73) Assignee: Siemens Aktiengesellschaft, Munich (DE)

( * ) Notice: Subject to any disclaimer, the term of this patent is extended or adjusted under 35 U.S.C. 154(b) by 548 days.

(21) Appl. No.: 11/084,516

(22) Filed: Mar. 17, 2005

(65) Prior Publication Data

US 2005/0207924 A1 Sep. 22, 2005

(30) Foreign Application Priority Data

Mar. 22, 2004 (DE) .................. 10 2004 013 921

(51) Int. Cl.
*G21K 1/00* (2006.01)
(52) U.S. Cl. ...................... 378/155; 378/154
(58) Field of Classification Search ................ 378/155, 378/154, 145, 147, 98.8
See application file for complete search history.

(56) References Cited

U.S. PATENT DOCUMENTS

| | | | |
|---|---|---|---|
| 2,062,562 A * | 12/1936 | Dent ........................... | 378/155 |
| 2,138,555 A | 11/1938 | Otvos | |
| 4,982,419 A | 1/1991 | Horikawa | |
| 5,305,369 A * | 4/1994 | Johnson et al. ............. | 378/155 |
| 5,559,851 A | 9/1996 | Schmitt | |
| 6,181,773 B1 * | 1/2001 | Lee et al. .................... | 378/155 |
| 6,795,528 B2 * | 9/2004 | Nokita ........................ | 378/155 |

FOREIGN PATENT DOCUMENTS

| | | |
|---|---|---|
| DE | 44 01 393 C1 | 1/1994 |
| DE | 698 05 733 | 5/1999 |
| EP | 0 913 838 B1 | 9/1998 |
| GB | 812077 | 4/1959 |

OTHER PUBLICATIONS

NL-Search Report dated Oct. 16, 2007.

* cited by examiner

*Primary Examiner*—Irakli Kiknadze
(74) *Attorney, Agent, or Firm*—Brinks Hofer Gilson & Lione

(57) ABSTRACT

In a diagnostic X-ray system having a scattered radiation grid driven via a wobble bearing, restoring forces generated via the wobble bearing and hence the vibration on the diagnostic X-ray system are minimized while simultaneously requiring a minimal space. A plate-like compensatory mass disposed parallel to the scattered radiation grid is provided, which during operation executes a linear motion that is contrary to the linear motion of the scattered radiation grid.

20 Claims, 2 Drawing Sheets

APPARATUS FOR DRIVING A SCATTERED RADIATION GRID OF A DIAGNOSTIC X-RAY SYSTEM

FIELD

The present invention relates, generally, to an apparatus for driving a plate-like driven mass, and more particularly, to an apparatus for driving a scattered radiation grid of a diagnostic X-ray system having a drive unit and a wobble bearing for converting and transmitting a rotary motion of the drive unit into a linear motion of the driven mass.

BACKGROUND

An apparatus for driving a scattered radiation grid of a diagnostic X-ray system is known for instance from German Patent 44 01 939 C1.

In a diagnostic radiology system, in particular a diagnostic X-ray system, a scattered radiation grid is disposed between a radiation source and a detection element, such as an X-ray film. This scattered radiation grid typically has a plurality of individual laminations and serves to absorb the scattered radiation that occurs when radiation is passed through an object to be irradiated, in particular a part of a human body. Image quality is enhanced because of the absorption of the scattered radiation. If the scattered radiation grid with the individual laminations of absorbent material is disposed in stationary fashion, such arrangement may produce interfering lines or marks on the X-ray film. The scattered radiation grid is therefore typically put into linear motion. From DE 44 01 939 C1, a tumbling or wobble bearing is provided. For a comparatively simple construction, the wobble bearing brings about a uniform motion of the scattered radiation grid even at the turning point.

One such scattered radiation grid has a mass of up to several kilograms. By way of the wobble bearing and the drive unit, in particular a controllable electric motor, restoring forces are therefore transmitted to a corresponding mount and hence to the entire diagnostic X-ray system. The forces can cause vibrations that adversely affect the image sharpness.

In German Patent Disclosure DE 698 05 733 T2, a diagnostic X-ray system can be found in which the scattered radiation grid is moved with the aid of a stepping motor. The transmission of motion is effected via a crank and a connecting rod. Electrical control of the stepping motor is necessary to assure a uniform linear motion even at the turning points of the crank. A second crank and a second connecting rod on the motor also provide a counterweight for compensating for mass in order to prevent interfering vibration.

Typically, modern diagnostic X-ray systems have a compact structure. The installation space for the scattered radiation grid is therefore limited.

OBJECT AND SUMMARY

The present invention is defined by the appended claims. This description summarizes some aspects of the present embodiments and should not be used to limit the claims.

A scattered radiation grid is driven, in particular, via a wobble bearing with minimal vibration while using minimal space.

An apparatus is provided having a drive unit and a wobble bearing for converting and transmitting a rotary motion of a drive unit into a linear motion of the scattered radiation grid. Further, via the wobble bearing, a likewise plate-like compensatory mass, disposed parallel to the scattered radiation grid, is mechanically coupled in such a way that during operation, the compensatory mass executes a linear motion that is contrary to the linear motion of the scattered radiation grid.

The required space is minimized by a geometric design of the compensatory mass, corresponding approximately to that of the scattered radiation grid, and the guidance or linear motion being parallel to that of the scattered radiation grid. The compensatory mass and the scattered radiation grid are accordingly guided in two planes parallel to one another. As such, the requisite installation space for the compensatory mass is reduced. Moreover, a comparatively simple compensation of mass to eliminate interfering vibrations is attained even with the complicated tumbling motion executed by the wobble bearing. The compensatory mass desirably has a substantially similar or equal mass to the scattered radiation grid acting as a driven mass. Because of this design, with a comparatively simple configuration, an effective reduction of the forces acting on the drive unit is attained while requiring minimal space.

Desirably, the scattered radiation grid is connected to the wobble bearing via a thrust rod and at least one decoupling element which converts the tumbling motion exerted by the wobble bearing into a linear motion. Via the thrust rod, a simple, mechanically rigid connection is attained, assuring by the at least one decoupling element that the complicated, three-dimensional tumbling motion is converted into a relatively simple linear motion of the compensatory mass.

Desirably, the wobble bearing is connected to the scattered radiation grid via a coupling element, such as a peg or protrusion, while the thrust rod extends approximately along the side of the coupling element. Furthermore, a first end of the thrust rod is connected to the wobble bearing substantially diametrically opposite the coupling element. As such, the thrust rod engages the wobble bearing in terms of force diametrically opposite the coupling element yet extends approximately along the side of the coupling element to the compensatory mass. In particular, the thrust rod here may bypass the wobble bearing in the region of the coupling element. By this provision, effective mass compensation is achieved because of the diametrically opposed engagement points of the coupling element and the thrust rod, so that a central axis of the wobble bearing is substantially free of force and hence low in vibration. Further, by this provision, a substantially compact construction may be attained since the thrust rod does not increase the required installation space. This installation space is formed substantially by the diameter of the wobble bearing, plus the approximately radially protruding peg. Within this effective cross section formed by the wobble bearing and the peg, the thrust rod is guided without requiring additional space. The forces absorbed or exerted via the thrust rod are therefore guided from the underside of the wobble bearing diametrically opposite the coupling element along the top side toward the compensatory mass.

For a desirably easy attachment of the thrust rod, a retaining element may be secured to the wobble bearing and may be clamped onto the wobble bearing. The retaining element has a connection part for receiving the first end of the thrust rod. Because the retaining element can be clamped on, a conventional wobble bearing may be used without any substantial structural change. The retaining element, configured desirably as a retaining ring, is simply placed on a conventional wobble bearing for attaching the thrust rod.

The thrust rod is supported in the connection part via a first joint head. This joint head forms a first decoupling element for converting the tumbling motion into a linear motion.

The thrust rod is connected by its second end to a guide carriage or sled, or the like, which for transmitting the linear motion to the compensatory mass is secured to the compensatory mass. A bearing element is provided, which can be configured as a revolving ball system which on one side is supported slidingly in the guide carriage and on the other side is connected to the thrust rod. The bearing element makes a motion of the second end of the thrust rod in a direction different from that of the linear motion of the compensatory mass. The bearing element may be supported perpendicular to the linear motion of the compensatory mass and thus may make a linear compensatory motion possible. The bearing element supported in the guide carriage may thus form a second decoupling element.

As a third decoupling element, a second joint head is provided, by way of which the thrust rod is connected by a second end to the guide carriage. This second joint head is supported in the bearing element, so that this bearing element simultaneously includes both the second and the third coupling element.

To enable a secure guidance of the thrust rod even over a relatively long distance, the thrust rod is supported inside a bearing housing, and the bearing housing is secured to a frame component or housing component.

The apparatus described herein is utilized in a diagnostic radiology system, in particular a diagnostic X-ray system. The mass compensation described for a wobble bearing can in principle be employed with other applications using wobble bearings as well.

Illustrative and exemplary embodiments of the invention are described in further detail below with reference to and in conjunction with the figures.

BRIEF DESCRIPTION OF THE DRAWINGS

In the drawings, parts that function the same are identified by the same reference numerals.

Figure 1:
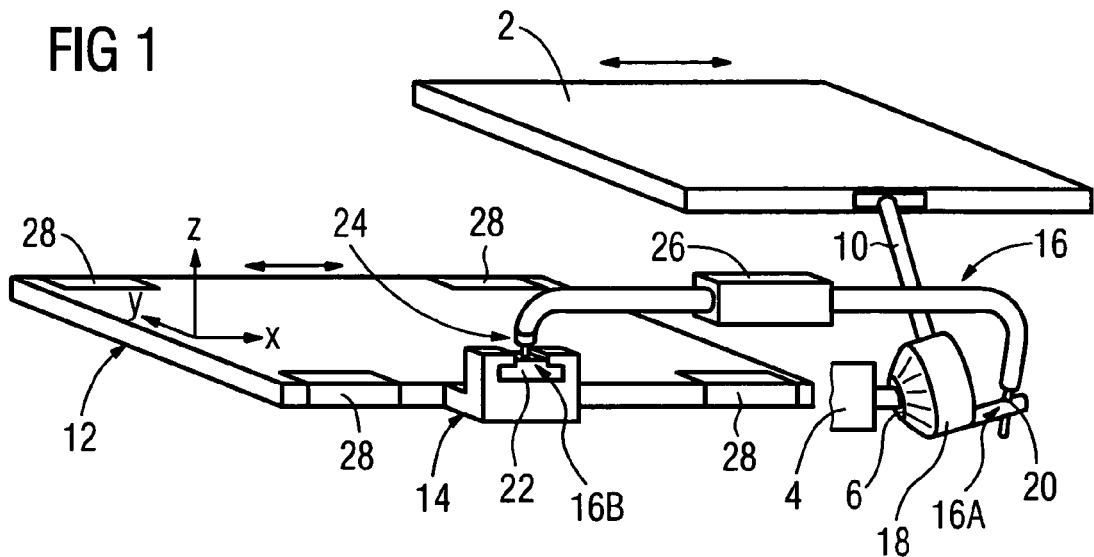
FIG. 1 is a perspective, fragmentary view of the coupling of both a driven mass, configured as a scattered radiation grid, and a compensatory mass on a wobble bearing.

The apparatus shown in FIG. 1 includes a scattered radiation grid 2, which forms a driven mass and is set into a linear motion, as represented by the double arrow, via a controllable electric motor 4, only part of which is shown, and via a wobble bearing 6. For coupling the scattered radiation grid 2 to the wobble bearing 6, a coupling element 10 configured in the manner of a peg is provided. Via the wobble bearing 6, the rotary motion exerted by the electric motor 4 is converted into the linear motion.

The apparatus furthermore includes a compensatory mass 12, which is connected to the wobble bearing 6 via a mechanical rod linkage. A guide carriage 14, a thrust rod 16, and a retaining element 18 configured as a retaining ring, which is secured in a clamping fashion to the wobble bearing 6, are provided for coupling the compensatory mass 12 to the wobble bearing 6. A first end 16A of the thrust rod 16 is supported in the manner of a first joint head in a connection part 20 of the retaining element 18. The second end 16B of the thrust rod 16 is likewise supported on the order of a second joint head in a bearing element 22. The bearing element 22 is in turn supported in the guide carriage 14. The second end 16B having the joint head is configured here as a separate piece, as a threaded stopper 24, which can be screwed into the thrust rod 16. As such, the thrust rod 16 has a female thread and the threaded stopper 24 has a corresponding male thread as well as an engagement face for a polygonal or hexagonal wrench, or the like.

A bearing configured as a slide bearing housing 26, through which the thrust rod 16 is passed, is provided approximately near the middle of the thrust rod 16. The compensatory mass 12 has further bearing elements 28, with which the compensatory mass 12 is longitudinally displaceably guided in a guide rail 30A of a retaining profile section 32. (See FIG. 2).

Figure 2:
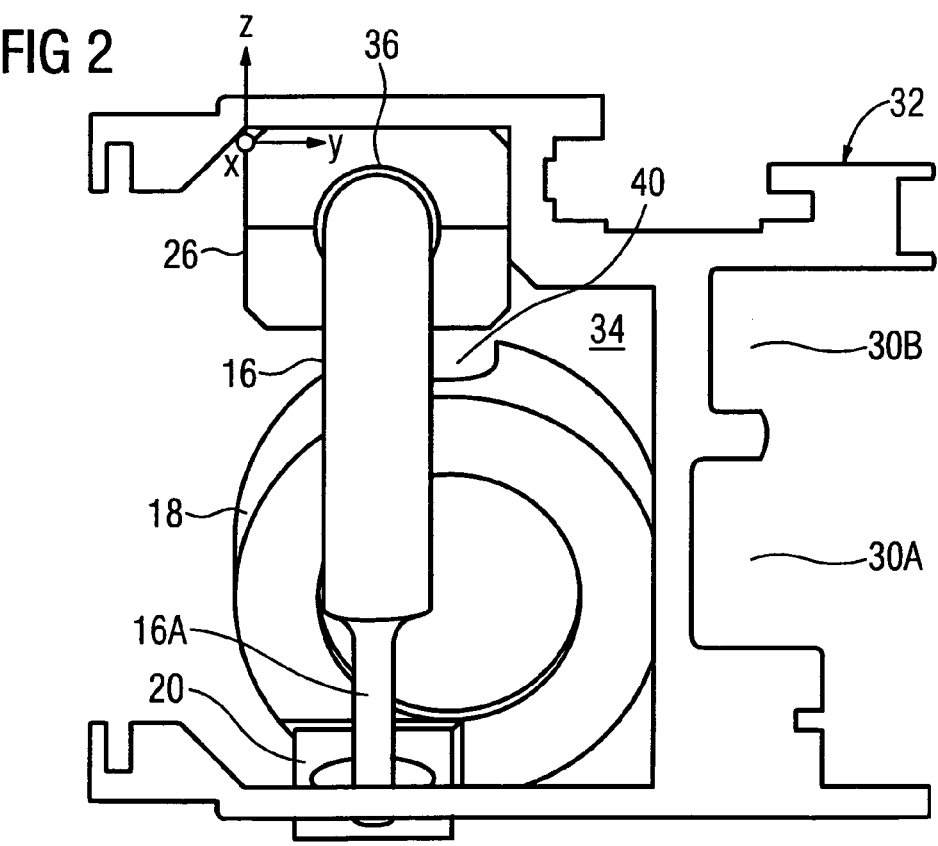
FIG. 2 is a partial cross section through a retaining profile section in the form of a frame component of a diagnostic X-ray system that is configured to receive the scattered radiation grid and the compensatory mass.

Shown in FIG. 2, above the first guide rail 30A for the compensatory mass 12, a second guide rail 30B is provided, in which the scattered radiation grid 2 is supported longitudinally displaceably. Diametrically opposite the retaining profile section 32 shown in FIG. 2, there is a further retaining profile section in which the second side of the compensatory mass 12 and of the scattered radiation grid 2 is supported. The compensatory mass 12 and the scattered radiation grid 2 therefore have substantially the same width and furthermore have a substantially comparable length. They are approximately comparable in shape and in particular also in their mass. The retaining profile section 32 moreover, on the outside facing away from the guide rails 30A, B, has a receiving chamber 34, in which the individual components for the mass compensation are disposed along with the electric motor 4 and the wobble bearing 6. FIG. 2 shows the retaining element 18 with the connection part 20, the thrust rod 16 with the second end 16B disposed in the retaining element 18, and the slide bearing housing 26 configured in two parts. For the sliding support in the slide bearing housing 26, a lubrication film or sliding film 36 is provided in particular. The slide bearing housing 26 is secured to the retaining profile section 32 by being screwed to it.

During operation, the rotary motion generated by the electric motor 4 is converted via the wobble bearing 6 into a tumbling motion. This tumbling motion is transmitted via the coupling element 10 to the plate-like scattered radiation grid 2 and converted into a linear motion, causing the scattered radiation grid to move back and forth in the guide rail 30B. Simultaneously, the tumbling motion is transmitted to the thrust rod 16. By way of the special coupling of the thrust rod 16 to the compensatory mass 12, the latter is put into linear motion. The linear motions of the scattered radiation grid 2 and of the compensatory mass 12 are contrary to one another. Via the three decoupling elements, namely the first end 16A configured as a joint head, the second end 16B configured as a joint head of the thrust rod 16, and the slide element 22, the decoupling from the three-dimensional tumbling motion is accomplished.

The two plate-like elements, namely the scattered radiation grid 2 and the compensatory mass 12, are located directly one above the other in the retaining profile section 32 and hence are disposed in a substantially maximum space-saving way. Because of the contrary linear motion, the restoring forces and restoring moments exerted on the electric motor 4 are kept substantially minimal, so that at most only minimal vibration is transmitted to the retaining profile section 32 and hence to the entire diagnostic X-ray system.

As shown in FIG. 2, the receiving chamber 34 is substantially limited in size. The thrust rod is first guided upward from the lower end of the retaining element 18 along the face end of the wobble bearing 6 and is then bent by approximately 90° and extends in the upper region of the receiving chamber 34 above the wobble bearing 6 and the electric motor 4 to the guide carriage 14, toward which the thrust rod 16 is bent again by approximately 90° to form a wide U shape. The two bent end pieces 16A, 16B define a plane which extends substantially perpendicular to the planes of the plate-like elements 2, 14.

Figure 3:
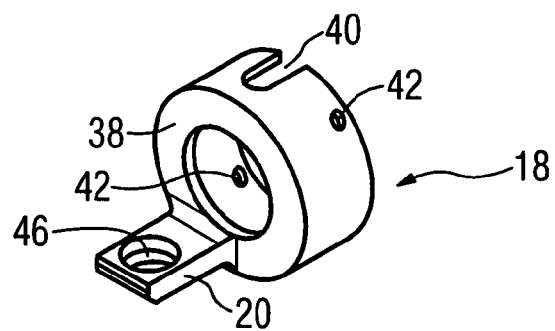
FIG. 3 is a perspective view of a ring-like retaining element, which is configured to be clamped onto the wobble bearing.

As shown in FIG. 3, the retaining element 18 is configured on the order of a ring, with a boundary or limiting ring 38 on a face end, and with the connection part 20 integrally formed onto the boundary ring. The connection part 20 is located in the vicinity of an outer circumference of the retaining element 18, specifically diametrically opposite a recess 40, through which the coupling element 10 of the wobble bearing 6 may be passed. The retaining element 18 is slipped onto the wobble bearing 6 and then fixed in a clamping fashion to the wobble bearing with screws or the like. For this purpose, screw openings 42 with female threads are provided.

Figure 4:
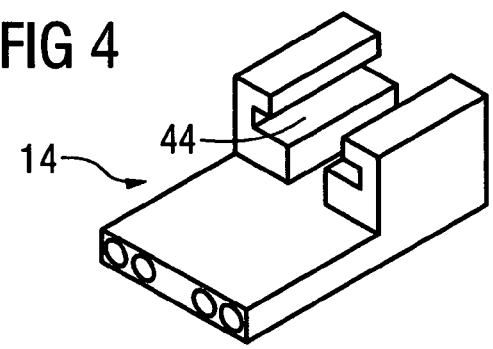
FIG. 4 is a guide carriage shown in a perspective view, by way of which the thrust rod is attached to the compensatory mass.
Figure 5:
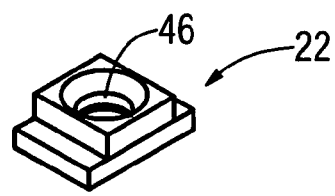
FIG. 5 is a slide element in a perspective view, configured to be received in the guide carriage of FIG. 4.

As shown in FIG. 4, the guide carriage 14 includes a T-shaped receiving profile section 44. The outer contour of the slide element 22 shown in FIG. 5 is complementary to this receiving profile section 44. The slide element 22 furthermore has a bore 46, whose upper peripheral region forms a funnel-shaped or spherical surface to enable a connection, in particular in the form of a ball joint, together with the second end 16B of the thrust rod 16. In the same way as the bearing element 22, the connection part 20 also has such a bore 46.

Figure 6:
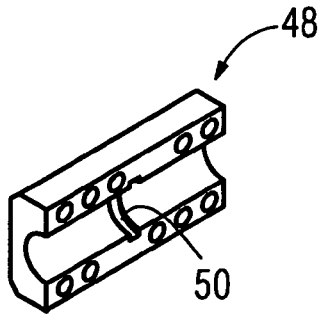
FIG. 6 is one half of a two-part slide bearing housing, seen in a perspective view.

The bearing housing 26 is formed of two slide bearing halves 48, one of which is shown in FIG. 6. The two halves are braced on one another on diametrically opposed flanges. Through the opposed flanges, bores are provided for mutually securing them, that is, for securing the slide bearing housing 26 to the retaining profile section 32. In the middle of the approximately semicircular recess in the slide bearing half 48 shown, a groove 50 is configured along a radial semicircle, and a corresponding spring of the lubrication film 36 engages groove 50 to secure against axial slippage inside the slide bearing housing 26.

We claim:

1. An apparatus for driving a plate-like driven mass, comprising:
   a drive unit;
   a wobble bearing to convert a rotary motion of the drive unit into a linear motion of the driven mass; and
   a plate-like compensatory mass disposed parallel to the plate-like driven mass, the compensatory mass mechanically coupled with the wobble bearing so as to move linearly contrary to a linear motion of the plate-like driven mass during operation of the drive unit.

2. The apparatus of claim 1, wherein the plate-like driven mass is a scattered radiation grid of a diagnostic X-ray system.

3. The apparatus of claim 1, wherein the compensatory mass is connected to the wobble bearing via a thrust rod and at least one decoupling element which converts the tumbling motion exerted by the wobble bearing into the contrary linear motion.

4. The apparatus of claim 3, wherein the thrust rod is connected by a second end to a guide carriage secured to the compensatory mass.

5. The apparatus of claim 4, further comprising a bearing element, supported on one side in the guide carriage and connected on the other side to the thrust rod for permitting a linear compensatory motion.

6. The apparatus of claim 5, wherein the linear compensatory motion is perpendicular to the linear motion of the compensatory mass.

7. The apparatus of claim 5, wherein the thrust rod is connected by the second end to the guide carriage via a second joint head.

8. The apparatus of claim 7, wherein the trust rod is supported in the bearing element.

9. The apparatus of claim 4, further comprising a bearing housing in which the thrust rod is supported in sliding fashion and which is secured to a frame component or housing component.

10. The apparatus of claim 3, further comprising a bearing housing in which the thrust rod is supported in sliding fashion and which is secured to a frame component or housing component.

11. The apparatus of claim 3 further comprising a retaining element secured to the wobble bearing, and having a connection part to receive a first end of the thrust rod.

12. The apparatus of claim 3, wherein the wobble bearing is connected to the driven mass via a coupling element, and the thrust rod extends along a side of the coupling element.

13. The apparatus of claim 12, wherein the coupling element is a peg.

14. The apparatus of claim 12, wherein a first end of the thrust rod is connected to the wobble bearing in a diametrically opposite configuration to the coupling element.

15. The apparatus of claim 14, further comprising a retaining element secured to the wobble bearing, and having a connection part to receive a first end of the thrust rod.

16. The apparatus of claim 15, wherein the retaining element is clamped to the wobble bearing.

17. The apparatus of claim 15, wherein the thrust rod is supported in the connection part via a first joint head.

18. The apparatus of claim 17, wherein the first joint head is one decoupling element of a plurality of decoupling elements configured for converting a tumbling motion into the linear motion.

19. A diagnostic radiology system having an apparatus for driving a scattered radiation grid, the apparatus comprising:
   a drive unit;
   a wobble bearing to convert and transmit a rotary motion of the drive unit into a linear motion of the scattered radiation grid, and
   a compensatory mass disposed generally in parallel to the scattered radiation grid, the compensatory mass being mechanically connected with the wobble bearing so as to execute during operation of the drive unit a linear motion that is contrary to a linear motion of the scattered radiation grid.

20. The diagnostic radiology system of claim 19, wherein the compensatory mass is connected to the wobble bearing via a thrust rod and at least one decoupling element which converts the tumbling motion exerted by the wobble bearing into the contrary linear motion.

* * * * *